United States Patent [19]

Haughan et al.

[11] Patent Number: 5,792,774
[45] Date of Patent: Aug. 11, 1998

[54] QUINOLONES AND THEIR THERAPEUTIC USE

[75] Inventors: Alan Findlay Haughan; Steven Colin Beasley; John Gary Montana; Robert John Watson, all of Cambridge, United Kingdom

[73] Assignee: Chiroscience Limited, Cambridge, United Kingdom

[21] Appl. No.: 803,731

[22] Filed: Feb. 21, 1997

[30] Foreign Application Priority Data

Feb. 21, 1996 [GB] United Kingdom .............. 9603654
Feb. 21, 1996 [GB] United Kingdom .............. 9603655
Feb. 21, 1996 [GB] United Kingdom .............. 9603689

[51] Int. Cl.$^6$ ............... A61K 31/435; C07D 221/06
[52] U.S. Cl. ............................... 514/294; 546/94
[58] Field of Search ................ 546/94, 95; 514/294

[56] References Cited

U.S. PATENT DOCUMENTS 4,001,243  1/1977  Gerster ............................ 260/287 P
4,317,820  3/1982  Ishikawa et al. .................... 424/246
4,416,884  11/1983  Ishikawa et al. .................... 424/250

FOREIGN PATENT DOCUMENTS 1433151  4/1976  United Kingdom .
2236751  4/1991  United Kingdom .

*Primary Examiner*—Joseph McKane
*Attorney, Agent, or Firm*—Saliwanchik, Lloyd & Saliwanchik

[57] ABSTRACT

A compound of formula (I)

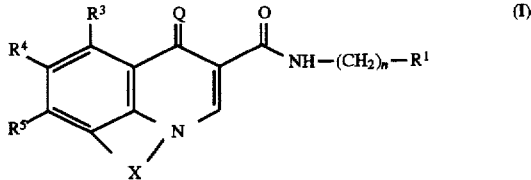

or a pharmaceutically-acceptable salt, solvate or hydrate thereof.

23 Claims, No Drawings

QUINOLONES AND THEIR THERAPEUTIC USE

FIELD OF THE INVENTION

The present invention relates to novel quinolone derivatives and pharmaceutically-acceptable salts thereof, processes for their production, and their formulation and use as pharmaceuticals.

BACKGROUND OF THE INVENTION

Quinolone and quinolizine compounds are known mainly as antibacterial agents (JP-A-05025162; U.S. Pat. No. 5,037, 834; EP-A-0420069; JP-A-02040379; EP-A-0343560; DE-A-3816119; EP-A-0304158; FR-A-2644784; WO-A-9410163; DE-A-3641312) or antiviral agents (U.S. Pat. No. 4,959,363), but also as inhibitors of 5-lipoxygenase (JP-A-02124871), cardiotonics and vasodilators (JP-A-01061461) and 5-$HT_3$ antagonists for the treatment of peripheral disorders associated with pain (WO-A-9501793; GB-A-2236751).

GB-A-2236751 describes quinolone-3-carboxamides as 5-$HT_3$ antagonists, for use in the treatment of neuropsychiatric disorders. U.S. Pat. No. 4,001,243 discloses benzoquinoline-2-carboxylic acids and esters as antimicrobial agents. GB-A-1433151 discloses N-tetrazolyl-benzoquinolizine-2-carboxamides, as agents that may be useful in the treatment of allergies including asthma.

Phosphodiesterases (PDE) and Tumour Necrosis Factor (TNF), their modes of action and the therapeutic utilities of inhibitors thereof, are described in WO-A-9704775 and WO-A-9704779, the contents of which are incorporated herein by reference. The same documents disclose quinolones having utility as PDE and TNF inhibitors.

SUMMARY OF THE INVENTION

This invention relates to compounds and their utility to treat disease states, for example disease states associated with proteins that mediate cellular activity, for example by inhibiting tumour necrosis factor and/or by inhibiting phosphodiesterase IV. According to the invention, novel compounds are of formula (I):

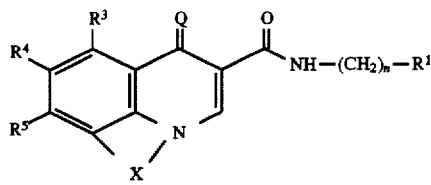

wherein n is 1, 2 or 3;

$R^1$ represents cycloalkl, aryl, heteroaryl or heterocyclo, in which any ring may be fused to a second ring selected from aryl and heteroaryl, to give a bicyclic structure, and in which any group is optionally substituted by one or more substituents chosen from halo, $C_{1-6}$ alkoxy, hydroxy, CN, $CO_2H$ (or $C_{1-6}$ alkyl esters or $C_{1-6}$ alkyl amides thereof), $C_{1-6}$ alkyl, $NR^6R^7$ and $SO_2NR^6R^7$;

$R^3$, $R^4$ and $R^5$ are the same or different and represent H, halo, $C_{1-6}$ alkoxy, hydroxy, CN, $CO_2H$ (or $C_{1-6}$ alkyl esters or $C_{1-6}$ alkyl amides thereof), $NR^6R^7$, $SO_2NR^6R^7$ or $C_{1-6}$ alkyl in which alkyl is optionally substituted with halo, $C_{1-6}$ alkoxy, hydroxy, CN, $CO_2H$ (or $C_{1-6}$ alkyl esters or $C_{1-6}$ alkyl amides thereof), $NR^6R^7$ or $SO_2NR^6R^7$, or any adjacent two substituents $R^3$-$R^5$ are joined to form an optionally substituted carbocyclic aromatic, heteroaromatic, saturated carbocyclic or heterocyclic ring;

$R^6$ and $R^7$ are the same or different and represent H, $C_{1-6}$ alkyl, cycloalkyl, $C_{1-6}$ alkylcarbonyl, arylcarbonyl, $C_{1-6}$ alkoxycarbonyl, arylsulphonyl or $C_{1-6}$ alkylsulphonyl or $NR^6R^7$ is a 5 or 6-membered ring such as pyrrolidine, piperidine, morpholine or piperazine;

X represents a linking group selected from —$(CR^9R^{10})_{2-3}$—, —Y—$(CR^9R^{10})_2$—, —$(CR^9R^{10})_2$—Y—, —$CR^9R^{10}$—Y—$CR^9R^{10}$— and —Y—$CR^9R^{10}$—Z—, Y and Z being independently $NR^{11}$, O or $S(O)_{0-2}$, provided that Y and Z are not both $S(O)_{0-2}$;

Q represents O or S; and each $R^9$, each $R^{10}$ and $R^{11}$ are the same or different and are H or $C_{1-6}$ alkyl;

and pharmaceutically-acceptable salts, solvates and hydrates thereof

Combinations of substituents and/or variables are only permissible if such combinations result in stable compounds.

DESCRIPTION OF THE INVENTION

Suitable pharmaceutically-acceptable salts are pharmaceutically-acceptable base salts and pharmaceutically-acceptable acid addition salts. Certain of the compounds of formula (I) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (I) which contain an amino group form acid addition salts. Suitable acid addition salts include pharmaceutically-acceptable inorganic salts such as the sulphate, nitrate, phosphate, borate, hydrochloride and hydrobromide and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (I) are prepared using conventional procedures.

It will be appreciated by those skilled in the art that some compounds of formula (I) can exist in more than one tautometric form. This invention extends to all tautomeric forms.

It will be appreciated that some of the compounds according to the invention can contain one or more asymmetrically-substituted carbon and/or sulphur atoms. The presence of one or more of these asymmetric centers in a compound of formula (I) can give rise to stereoisomers, and in each case the invention is to be understood to extend to all such stereoisomers, including enantiomers, and diastereoisomers and mixtures, including racemic mixtures, thereof.

When used herein the term alkyl whether used alone or when used as part of another group includes straight and branched chain alkyl groups. Cycloalkyl includes a non-aromatic cyclic or multicyclic ring system of about 3 to 10 carbon atoms. The cyclic alkyl may optionally be partially unsaturated. Alkoxy means an alkyl-O-group in which the alkyl group is as previously described. Alkyl amide includes both monoalkyl and dialkyl amides, in which the alkyl groups (previously defined) may be the same or different. Alkylcarbonyl means an alkyl-CO-group in which the alkyl group is as previously described. Aryl indicates carbocyclic radicals containing about 6 to 10 carbon atoms. Heteroaryl means an about 5 to about 10-membered aromatic monocyclic or multicyclic ring system in which one or more of the atoms in the ring system is an element other than carbon, chosen from amongst nitrogen, oxygen or sulphur. Heterocyclo means an about 5 to about 10-membered saturated or partially saturated monocyclic or multicyclic ring system in which one or more of the atoms in the ring system is an element other than carbon, chosen from amongst nitrogen, oxygen or sulphur. Arylcarbonyl means an aryl-CO-group. Arylsulphonyl means an aryl-$SO_2$- group. Alkylsulphonyl means an alkyl-$SO_2$-group. Alkoxycarbonyl means an alkoxy-CO-group. When any two of $R^3$, $R^4$ and $R^5$ are joined together, an example is methylenedioxy ($OCH_2O$). Halo means fluorine, chlorine, bromine or iodine.

The compounds of formula (I) are preferably in pharmaceutically-acceptable form. By pharmaceutically-acceptable form is meant, inter alia, a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%.

Compounds of the invention can be used in the prevention or treatment of "TNF-mediated disease or disease states", i.e. any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are considered to be inhibited by compounds of the present invention and thus are herein referred to collectively as "TNF" unless specifically indicated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (I) or a pharmaceutically-acceptable salt thereof.

PDE IV inhibitors are useful in the treatment of a variety of allergic and inflammatory diseases, including: asthma, chronic bronchitis, atopic dermatitis, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia PDE IV inhibitors are also useful in conditions ameliorated by neuroprotectant activity, such as cardiac arrest, stroke and intermittent claudication. PDE IV inhibitors may be useful in the treatment of tardive dyskinesia, ischaemia and Huntingdon's disease. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (I). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HV), which comprises administering to such mammal an effective TNF-inhibiting amount of a compound of Formula (I) or a pharmaceutically-acceptable salt thereof.

The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to, feline immunodeficiency virus (FIV) and other retroviral infections such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

Compounds of the invention may also suppress neurogenic inflammation through elevation of cAMP in sensory neurones. They are, therefore, analgesic, anti-tussive and anti-hyperalgesic in inflammatory disease associated with irritation and pain.

Compounds of the general formula (I) may be prepared by any suitable method known in the art and/or by the following process, which itself forms part of the invention.

In the description and formulae below the groups $R^1$, $R^3$, $R^4$, $R^5$, $R^6$, $R^7$, $R^9$, $R^{10}$, $R^{11}$, Q, X and Z are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionalities will be apparent to those skilled in the art. For specific details see "Protective Groups in Organic Synthesis", Wiley Interscience, T W Greene, PGM Wuts. Thus a process for preparing compounds of formula (I) in which, say, $R^4$ is $CO_2H$ comprises deprotecting (for example by hydrolysis) a compound of formula (I) in which $R^4$ is $CO_2R$ wherein R represents a suitable protecting group (e.g. methyl).

A preferred embodiment of formula (I) comprises those compounds wherein X is $(CR^9R^{10})_3$.

A process for preparing compounds of general formula (I) comprises coupling an acid of formula (II)

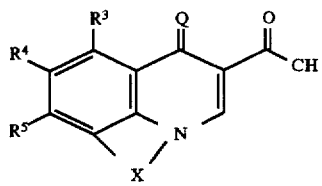

or an activated derivative thereof, with an amine of formula (III)

$NH_2-(CH_2)_n-R^1$ (III)

Amines of formula (III) are commercially available or can be readily obtained from commercially-available starting materials using methods known to those skilled in the art. Some of the amines of formula (III) are conveniently prepared by reductive amination of an appropriate carbonyl compound with a suitable amine. This amination may be carried out under any suitable standard conditions known to those skilled in the art. Active derivatives of acids of formula (II) include, for example, acid anhydrides and acid halides, such as acid chlorides.

The coupling reaction may be performed using standard conditions for amination reactions of this type. Thus, the reaction may be achieved in a solvent, for example an inert organic solvent such as an ether, e.g. a cyclic ether such as tetrahydrofuran, an amide, e.g. a substituted amide such as dimethylformamide, or a halogenated hydrocarbon such as dichloromethane, at a low temperature, e.g. −30° C. to ambient temperature, such as −20° C. to 0° C., optionally in the presence of a base, e.g. an organic base such as an amine, e.g. triethylamine or a cyclic amine such as N-methylmorpholine. The reaction may additionally be performed in the presence of a condensing agent, for example a diimide such as N,N-dicyclohexylcarbodiimide, advantageously in the presence of a triazole such as 1-hydroxybenzotriazole. Alternatively, the acid may be reacted with a chloroformate, for example ethyl chloroformate, prior to reaction with the amine of formula (III).

Acids of general formula (II) may be prepared according to the procedure described in EP-A-0373531, DE-A-0683169 or by Kaminsky and Meltzer, *J. Med. Chem.*, 11:160–164 (1968). This procedure includes hydrolysis of the corresponding ester of general formula (IV)

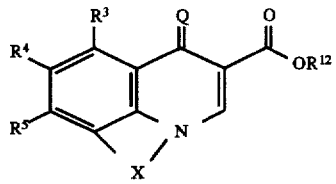

where $R^{12}$ represents an (ar)alkyl group such as methyl, ethyl, benzyl or tert-butyl.

Compounds of formula (IV) in which Q=S may be derived from the corresponding compounds where Q=O using standard conditions for sulphurisation of such compounds. For example, suitable conditions comprise reaction with phosphorus pentasulphide ($P_4S_{10}$) in an organic solvent such as pyridine at an appropriate temperature. The reflux temperature of the solvent is preferred.

Esters of general formula IV wherein X is $-Y'-CR^9R^{10}-Z'$, $Y'$ and $Z'$ each being $NR^{11}$, O or S, e.g. $-O-CR^9R^{10}-NR^{11}-$, may be prepared by cyclisation of intermediates of general formula (V)

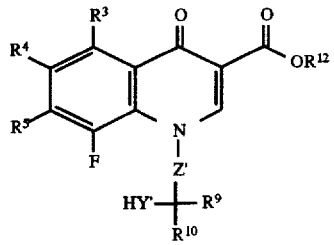

using procedures evident to those skilled in the art; for example, cyclisation may utilise a tetraalkylammonium fluoride such as tetrabutylammonium fluoride as reagent. $Y'$ or $Z'$ as S may subsequently be converted to SO or $SO_2$.

Intermediates of general formula (V) may be prepared by formylation of a corresponding amine or other intermediate of general formula (VI)

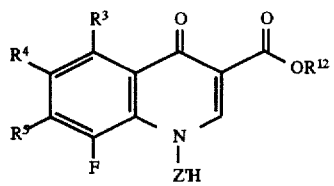

using, for example, formaldehyde.

Compounds of general formula (VI) may be prepared from the corresponding protected compounds of general formula (VII)

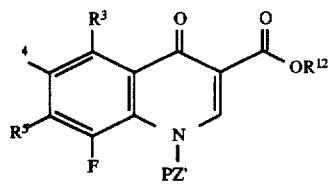

wherein P is any suitable protecting group, e.g. Boc, by deprotection using methods evident to those skilled in the art, such as reaction with base.

The quinoline nucleus in the above compounds may be generated by reaction of an ester of formula (VIII)

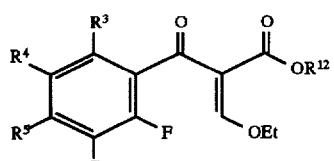

with an amine of general formula (IX)

$H_2N-Z'P$ (IX)

Intermediates of general formula (VIII) may be made from benzoic acids of general formula (X)

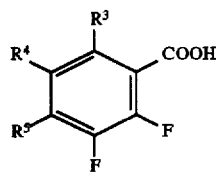

using methodology analogous to that reported previously (J. Med. Chem. 34:1142 (1991)).

When X is $-CR^9R^{10}-Y'-CR^9R^{10}-$, esters of general formula (IV) may be prepared from the corresponding intermediate of general formula (XI)

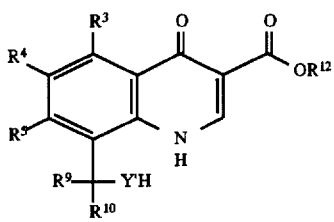
(XI)

by reaction with a formate derivative of general formula (XII)

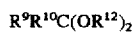
(XII)

Compounds of general formula (XI) may be prepared by hydrolysis of the corresponding intermediates (XIII)

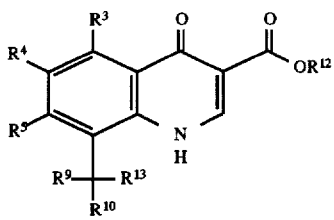
(XIII)

wherein $R^{13}$ represents a protected form of Y'H such as OAc, SAc or $NR^{11}Boc$.

The quinoline nucleus in the compounds (IV) and (XIII) may be generated by cyclisation of an ester of formula (XIV) or (XV)

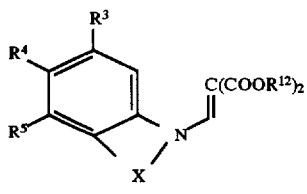
(XIV)

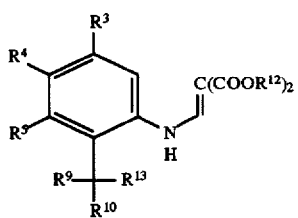
(XV)

using methodology analogous to that described by Kaminsky and Meltzer, supra. Suitable conditions include, for example, heating to reflux in diphenyl ether or a eutectic mixture of diphenyl ether and biphenyl.

Compounds of formula (XIV) or (XV) may be prepared by the reaction of an aniline of general formula (XVI) or (XVII)

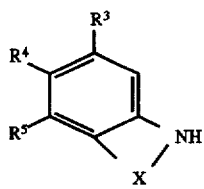
(XVI)

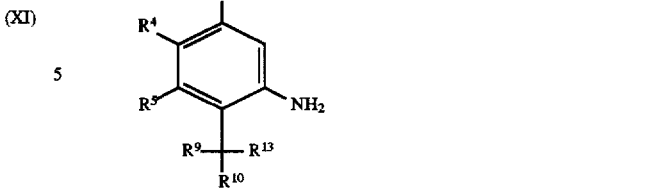
(XVII)

with a dialkl alkoxyethylidinemalonate of the formula (XVIII)

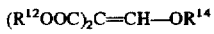
(XVIII)

wherein $R^{14}$ is a lower alkyl group such as methyl or ethyl. This reaction may be carried out under suitable standard conditions known to those skilled in the art, for example those described by Kaminsky and Meltzer, supra. For example, the reaction may be carried out at elevated temperature, for example 80°–150° C., in an inert solvent (such as xylene) or, preferably, in the absence of solvent.

Intermediates of formulae (IX), (X), (XII), (XVI), (XVII) and (XVIII) are commercially available or can be readily obtained from commercially available starting materials using methods known to those skilled in the art.

Compounds of formula (I) may also be prepared by interconversion of other compounds of formula (I). Thus, for example, a compound of formula (I) wherein $R^4$ is $C_{1-6}$ alkoxy may be prepared by appropriate alkylation of a compound of formula (I) wherein $R^4$ is a hydroxy group.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances. It will be appreciated that where a particular stereoisomer of formula (I) is required, this may be obtained by conventional resolution techniques such as high performance liquid chromatography. Where desired, however, appropriate homochiral starting materials may be used in the reaction sequence to yield a particular stereoisomer of formula (I).

A compound of formula (I) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (I) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose. Unit dose presentation forms for oral administration may be tablets and capsules and may contain conventional excipients such as binding agents, for example syrup, acacia, gelatin, sorbitol, tragacanth, or polyvinylpyrrolidone; fillers for example lactose, sugar, maize-starch, calcium phosphate, sorbitol or glycine; tabletting lubricants, for example magnesium stearate; disintegrants, for example starch, polyvinylpyrrolidone, sodium starch glycolate or microcrystalline cellulose; or pharmaceutically-acceptable wetting agents such as sodium lauryl sulphate.

Solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and, as desired, conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 µm, such as from 0.1 to 50 µm, preferably less than 10 µm, for example from 1 to 10 µm, 1 to 5 µm or from 2 to 5 µm. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to a suitable sterilising agent, before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (I), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (I) or if appropriate a pharmaceutically-acceptable salt thereon are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (I), or if appropriate a pharmaceutically-acceptable salt thereof, will comprise from about 0.5 to 20% by weight of the formulation, preferably from about 1 to 10%, for example 2 to 5%.

The dose of the compound used in the treatment of the invention may be determined by the skilled man, and will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kday, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically-acceptable" encompasses materials suitable for both human and veterinary use. No toxicological effects have been established for compounds of formula (I) in the above-mentioned dosage ranges.

The following Examples illustrate the invention.

EXAMPLE 1

9-fluoro-6,7-dihydro-5-methyl-N-[2-(4-pyridyl)ethyl]-1-oxo-1H,5H-benzo-[i,j]quinolizine-2-carboxamide Flumequine (0.46 g) and dichloromethane (16.3 ml) were combined under nitrogen and cooled to 0° C. Triethylamnine (0.27 ml) was then added dropwise, followed by isopropenyl chloroformate (0.21 ml) and the whole stirred for 60 minutes. 4-(2-Aminoethyl)pyridine (0.23 ml) was then added and the reaction stirred for 20 h, concentrated onto silica and purified by flash column chromatography to give the title compound (0.55 g) as a white solid.

11

TLC $R_f$=0.27 (5% MeOH/CH$_2$Cl$_2$) mp=217° C.

EXAMPLE 2

9-fluoro-6,7-dihydro-5-methyl-N-[2-(4-pyridyl)ethyl]-1-oxo-1H,5H-benzo-[i,j]quinolizine-2-carboxamide hydrochloride The product of Example 1 (393.2 mg) and chloroform (4 ml) were combined and stirred at room temperature. A solution of 1M hydrochloric acid in ether (1.08 ml) was then added and the resulting precipitate filtered and dried to give the title compound (433.4 mg) as a white solid. m.p.=268°–269° C.

$^1$HNMR (DMSO): 1.35(t, 3H), 2.1(m, 2H), 3.1(m, 4H), 3.7(m, 2H), 4.8(m, 1H),7.6–8.8 (7H, aromatic), 10.0(t,1H).

EXAMPLE 3

9-fluoro-6,7-dihydro-5-methyl-N-[(4-pyridyl)methyl]-1-oxo-1H,5H-benzo-[i,j]quinolizine-2-carboxamide Flumequine (0.46 g) and dichloromethane (16.3 ml) were combined under nitrogen and cooled to 0° C. Triethylamine (0.27 ml) was then added dropwise, followed by isopropenylchloroformate (0.21 ml) and the whole stirred for 60 minutes. 4-(Aminomethyl)pyridine (0.2 ml) was then added and the reaction stirred for 20 h, after which time it was diluted with dichloromethane, washed with water (3 times), dried (MgSO$_4$), concentrated in vacuo and triturated with acetone to give the title compound (0.49 g) as a yellow solid.

TLC $R_f$=0.43 (10% MeOH/CH$_2$Cl$_2$) m.p.=199°–200° C.

EXAMPLE 4

9-fluoro-6,7-dihydro-5-methyl-N-[(4-pyridyl)methyl]-1-oxo-1H,5H-benzo-[i,j]quinolizine-2-carboxamchloride hydrochloride Example 4 was conducted in a similar manner to Example 2. Thus 0.12 g of the product of Example 3 and 0.35 ml of a 1M solution of HCl in ether gave the title compound as an off-white solid. m.p.=251°–253° C.

1H NMR (DMSO): 1.35(t,3H), 2.1(m,2H), 3.2(m,2H), 4.8(m, 3H), 7.6–8.8(7H aromatic), 10.6(t,1H).

Assay Methods

PDE IV Inhibition Assay

The methods used to confirm the phosphodiesterase IV inhibitory activity of formula (I) are standard assay procedures, as disclosed by Schilling et al, An. Biochem. 216:154 (1994), Thompson and Strada, Adv. Cycl. Nucl. Res. 8:119 (1979), and Gristwood and Owen, Br. J. Pharmacol. 87:91P (1985). Compounds of formula (I) have exhibited activity at levels consistent with those believed to be useful in treating phosphodiesterase IV related disease states in those assays.

TNF Inhibition Assay

The ability of the compounds of formula (I) to inhibit TNF production in human monocytes is measured as follows. Peripheral blood mononuclear cells are prepared from freshly taken blood or "Buffy coats" by standard procedures. Cells are plated out in RPMI+1% foetal calf serum in the presence and absence of inhibitors. LPS (100 ng/ml) is added and cultures are incubated for 22 h at 37° C. in an atmosphere of 95% air/5% CO$_2$. Supernatants are tested for TNFα by ELISA using commercially available kits.

Skin Eosinophilia Model

In vivo activity in a skin eosinophilia model is determined by using the methods described by Hellewell et al Br. J. Pharmacol. 111:811 (1994) and Br. J. Pharmacol. 110:416 (1993). Activity in a lung model is measured using the procedures described by Kallos and Kallos Int. Archs. Allergy Appl. Immunol. 73:77 (1984) and Sanjar et al Br. J. Pharmacol. 99:679 (1990).

12

The following abbreviations have been used:
TNF tumour necrosis factor
LPS lipopolysaccharide (endotoxin)
ELISA enzyme linked immunosorbent assay Certain general description, and description relating to the preparation of intermediates, may be found in a copending Application, for the same assignee, having the same filing date.

We claim:

1. A compound of formula (I)

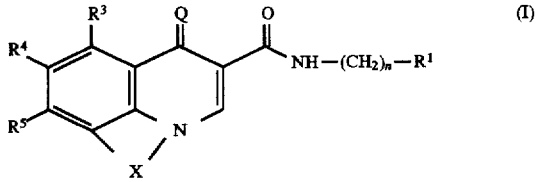

wherein n is 1, 2 or 3;

R$^1$ is selected from the group consisting of cycloalkyl, aryl, heteroaryl, and heterocyclo, any of which rings may be fused to a second ring selected from aryl, heteroaryl, to give a bicyclic structure, and in which the or each ring is optionally substituted by one or more substituents chosen from halo, C$_{1-6}$ alkoxy, hydroxy, CN, CO$_2$H, C$_{1-6}$ alkyl esters, C$_{1-6}$ alkyl amides, C$_{1-6}$ alkyl, NR$^6$R$^7$, and SO$_2$NR$^6$R$^7$;

R$^3$, R$^4$, and R$^5$ are the same or different and are selected from the group consisting of H, halo, C$_{1-6}$ alkoxy, hydroxy, CN, CO$_2$H, C$_{1-6}$ alkyl esters, C$_{1-6}$ alkyl amides, NR$^6$R$^7$, SO$_2$NR$^6$R$^7$ and C$_{1-6}$ alkyl in which alkyl is optionally substituted with halo, C$_{1-6}$ alkoxy, hydroxy, CN, CO$_2$H, C$_{1-6}$ alkyl esters, C$_{1-6}$ alkyl, NR$^6$R$^7$ or SO$_2$NR$^6$R$^7$, or any adjacent two substituents R$^3$–R$^5$ are joined to form an optionally substituted carbocyclic aromatic, heteroaromatic, saturated carbocyclic or heterocyclic ring;

R$^6$ and R$^7$ are the same or different and are selected from the group consisting of H, C$_{1-6}$ alkyl, cycloalkyl, C$_{1-6}$ alkylcarbonyl, arylcarbonyl, C$_{1-6}$ alkoxycarbonyl, arylsulphonyl, and C$_{1-6}$ alkylsulphonyl, or NR$^6$R$^7$ is a 5- or 6-membered ring selected from the group consisting of pyrrolidine, piperidine, morpholine, or piperazine;

X represents a linking group selected from the group consisting of —(CR$^9$R$^{10}$)$_{2-3}$—, —Y—(CR$^9$R$^{10}$)$_2$—, —(CR$^9$R$^{10}$)$_2$—Y—, —CR$^9$R$^{10}$—Y—CR$^9$R$^{10}$—, and —Y—CR$^9$R$^{10}$—Z—, Y and Z being independently selected from the group consisting of NR$^{11}$, O, and S(O)$_{0-2}$, provided that Y and Z are not both S(O)$_{0-2}$;

Q represents O or S;

each R$^9$, each R$^{10}$ and R$^{11}$ are the same or different and are H or C$_{1-6}$ alkyl;

or a pharmaceutically-acceptable salt, solvate, or hydrate thereof.

2. The compound, according to claim 1, wherein X is —Y—CR$^9$R$^{10}$—Z—.

3. The compound, according to claim 1, wherein X is —CR$^9$R$^{10}$—Y—CR$^9$R$^{10}$—.

4. The compound, according to claim 1, wherein X is selected from the group consisting of (CR$^9$R$^{10}$)$_q$, CR$^9$R$^{10}$CR$^9$R$^{10}$NR$^{11}$, NR$^{11}$CR$^9$R$^{10}$CR$^9$R$^{10}$, CR$^9$R$^{10}$CR$^9$R$^{10}$O, OCR$^9$R$^{10}$CR$^9$R$^{10}$, CR$^9$R$^{10}$CR$^9$R$^{10}$S(O)$_t$, and S(O)$_t$R$^9$R$^{10}$CR$^9$R$^{10}$, q=2–3 and t=0–2.

5. The compound, according to claim 4, wherein X is (CR$^9$R$^{10}$)$_3$.

6. The compound, according to claim 1, wherein Q is O.

7. The compound, according to claim 1, selected from the group consisting of
9-fluoro-6,7-dihydro-5-methyl-N-[2-(4-(2-pyridyl)ethyl]-1-oxo-1H,5H-benzo-[i,j]quinolizine-2-carboxamide and its hydrochloride, and
9-fluoro-6,7-dihydro-5-methyl-N-[(4-pyridyl)methyl]-1-oxo-1H,5H-benzo-[i,j]quinolizine-2-carboxamide and its hydrochloride.

8. The compound, according to claim 1, which has one or more chiral centres and is in the form of an enantiomer or diastereomer.

9. A pharmaceutical composition comprising a compound of claim 1, as active ingredient, in combination with a suitable excipient.

10. A method for treating a human or animal hosting a disease state capable of being modulated by inhibiting phosphodiesterase IV which comprises admninistering to said human or animal a disease-inhibiting amount of a compound of claim 1 in association with a pharmaceutically-acceptable carrier.

11. The method, according to claim 10, wherein the disease state is a pathological condition associated with a function of phosphodiesterase IV, eosinophil accumulation, or a function of eosinophil.

12. The method, according to claim 11, wherein the pathological condition is selected from the group consisting of asthma, chronic bronchitis, atopic dermatitis, allergic rhinitis, allergic conjunctivitis, vernal conjunctivitis, inflammation of the eye, allergic responses in the eye, eosinophilic granuloma, psoriasis, rheumatoid arthritis, gouty arthritis and other arthritic conditions, ulcerative colitis, Crohn's disease, adult respiratory distress syndrome, diabetes insipidus, keratosis, atopic eczema, atopic dermatitis, cerebral senility, multi-infarct dementia, senile dementia, memory impairment associated with Parkinson's disease, depression, cardiac arrest, stroke, and intermittent claudication.

13. The method, according to claim 11, wherein the pathological condition is selected from the group consisting of chronic bronchitis, allergic rhinitis, and adult respiratory distress syndrome.

14. The method, according to claim 10, wherein the disease state is capable of being modulated by TNF inhibition.

15. The method, according to claim 14, wherein the disease state is an inflammatory disease or autoimmune disease.

16. The method, according to claim 15, wherein the disease state is selected from the group consisting of joint inflammation, arthritis, rheumatoid arthritis, rheumatoid spondylitis and osteoarthritis, sepsis, septic shock, endotoxic shock, Gram-negative sepsis, toxic shock syndrome, acute respiratory distress syndrome, cerebral malaria, chronic pulmonary inflammatory disease, pulmonary sarcoidosis, asthma, bone resorption diseases, reperfusion injury, graft vs host reaction, allograft rejection, malaria, myalgias, HIV, AIDS, ARC, cachexia, Crohn's disease, ulcerative colitis, pyresis, systemic lupus erythematosus, multiple sclerosis, type 1 diabetes mellitus, psoriasis, Bechet's disease, anaphylactoid purpura nephritis, chronic glomerulonephritis, inflammatory bowel disease, and leukemia.

17. The method, according to claim 10, wherein the pathological condition or disease state is asthma.

18. The method, according to claim 16, wherein the disease state is selected from the group consisting of acute respiratory distress syndrome, pulmonary inflammatory disease, and pulmonary sarcoidosis.

19. The method, according to claim 16, wherein the disease state is selected from the group consisting of joint inflammation, arthritis, rheumatoid arthritis, rheumatoid spondylitis, and osteoarthritis.

20. The method, according to claim 14, wherein the disease state is a disease or disorder of the bran selected from the group consisting of brain trauma, ischaemia, Huntingdon's disease, and tardive dyskinesia.

21. The method, according to claim 14, wherein the disease state is a yeast or fungal infection.

22. A method for treating a human or animal in need of gastroprotection which comprises administering to said human or animal a gastroprotecting amount of a compound of claim 1 in association with a pharmaceutically-acceptable carrier.

23. A method for treating a human or animal in need of an analgesic, anti-tussive, or anti-hyperalgesic in the treatment of neurogenic inflammatory disease associated with irritation and pain which comprises administering to said human or animal an effective amount of a compound of claim 1 in association with a pharmaceutically-acceptable carrier.

* * * * *